(12) United States Patent
Calton et al.

(10) Patent No.: US 7,344,839 B2
(45) Date of Patent: Mar. 18, 2008

(54) VIRUS PREPARATIONS AND METHODS

(75) Inventors: Gary J. Calton, Elkridge, MD (US); Rita Fishelevich, Baltimore, MD (US)

(73) Assignee: AuRx, Inc., Elkridge, MD (US)

( * ) Notice: Subject to any disclaimer, the term of this patent is extended or adjusted under 35 U.S.C. 154(b) by 216 days.

(21) Appl. No.: 11/021,275

(22) Filed: Dec. 23, 2004

(65) Prior Publication Data
US 2006/0141566 A1 Jun. 29, 2006

(51) Int. Cl.
*C12Q 1/68* (2006.01)

(52) U.S. Cl. .................. 435/6; 435/69.1; 435/325; 435/235.1

(58) Field of Classification Search ............. 435/6, 435/69.1, 235.1, 325
See application file for complete search history.

(56) References Cited

U.S. PATENT DOCUMENTS

| | | | |
|---|---|---|---|
| 3,985,615 A | 10/1976 | Kubo | |
| 5,360,736 A | 11/1994 | Provost et al. | |
| 5,607,852 A | 3/1997 | Provost et al. | |
| 5,665,362 A | 9/1997 | inglis et al. | |
| 5,837,261 A | 11/1998 | Inglis et al. | |
| 6,013,265 A | 1/2000 | Aurelian | |
| 6,054,131 A | 4/2000 | Aurelian | |
| 6,267,967 B1 | 7/2001 | Johnston et al. | |
| 2003/0108860 A1* | 6/2003 | Reiter et al. ............ | 435/5 |

FOREIGN PATENT DOCUMENTS

| | | |
|---|---|---|
| DE | 209738 | 5/1984 |
| EP | 0573107 | 12/1993 |
| JP | 6-234659 | 8/1994 |

OTHER PUBLICATIONS

Wachsman et al. Vaccine, 2001, vol. 19, 1879-1890.*

* cited by examiner

*Primary Examiner*—Ali R. Salimi
(74) *Attorney, Agent, or Firm*—Knobbe Martens Olson & Bear LLP

(57) ABSTRACT

Methods are disclosed for the preparation of herpesvirus, such as herpes simplex virus type 2 for vaccine use. Such viruses can be grown on serum free or serum containing media and can be prepared from the virus containing culture supernatant or virus containing cells. The virus is prepared for subsequent pharmaceutical formulation by methods which may include treatment with solid phase affinity reagents containing sulfate- or sulfonate-comprising binding groups. Such sulfated polysaccharide groups as heparin or dextran sulfate may be used, and eluted with salt solutions. The process can be combined with other culture, harvesting and formulation steps.

16 Claims, No Drawings

VIRUS PREPARATIONS AND METHODS

CROSS-REFERENCE TO RELATED APPLICATIONS

Not Applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not Applicable.

BACKGROUND OF THE INVENTION (1) Field of the Invention

This invention relates to the production, the harvesting and the purification of virus from virus-infected cell cultures, for example for experimental and therapeutic purposes, e.g. for the production of pharmaceutical formulations such as prophylactic or therapeutic inoculations. In particular aspects, the invention relates to methods and arrangements for the production of preparations of herpesviruses. Other aspects of the invention will be apparent from the description given below.

(2) Description of the Related Art Including Information Disclosed Under 37 CFR 1.97 and 37 CFR 1.98.

Several methods are known for producing live virus preparations all of which include extraction of the virus from a virus infected cell, e.g. Vero cells or MRC5 cells among others, for vaccine, therapeutic and other purposes.

U.S. Pat. No. 3,985,615 (Osaka Research Foundation: T Kubo et al) shows production of live attenuated varicella virus for vaccine use by culture comprising passage in guinea pig primary embryonic tissue cells.

U.S. Pat. No. 5,024,836 (Merck: W J McAleer et al) relates to production of lyophilized vaccine preparations based thereon. Also disclosed is the fact that aqueous solutions of live virus vaccines are known to be unstable during storage.

DD-209738 (Cent Cerc Bioprep: IV Patrascu) illustrates production of another type of herpesvirus, for use as vaccine against Marek's disease. The herpesvirus is produced by (a) culturing specific-pathogen-free chicken embryo cells on dextran microspheres; (b) inoculating the culture at 80% confluence with turkey herpes virus strain FC-126 (clone 1, IIIb); (c) collecting the infected cells in SPGA medium (sucrose, phosphate, glutamate, bovine albumin fraction V) when the cytopathic effect is 80%; (d) subjecting the suspension to three ultrasonic pulses of 1 minute duration at 2 minute intervals and centrifuging it to recover a first crop of vaccine; (e) resuspending the sediment in SPCA medium and repeating step (d) to obtain a second crop of vaccine (to increase the vaccine yield by almost 2%); (f) freezing the combined vaccines at −100° C. prior to determining the virus titer; and (g) diluting the SPCA medium and freeze drying.

JP06234659-A (Z H Handai Biseibutsubyo Kenkyukai) describes, in an example, production of herpesviral vaccine on human diploid fibroblast MRC-5 cells cultured in MEM medium at 37° C., comprising inoculation of varicella virus Oka strain seed virus at a MOI of 0.03 to MRC-5 cells and culture at 37° C. for 2 days. Virus is then suspended in a solution containing 6.4 g NaCl, 0.16 g KCl, 2.3 g $Na_2HPO_4$ 12H2O, 0.16 g $KH_2PO_4$, 5 0.0 g sucrose, 1.0 g Na L-glutamate, 2.0 g gelatin, 25.0 g gelatin hydrolysate and 0.1 g EDA-3Na per L.

EP 0 573 107, U.S. Pat. No. 5,360,736 and U.S. Pat. No. 5,607,852 (Merck: P A Friedman et al) describe processes for production of attenuated varicella zoster virus vaccine, including a process for preparing live, attenuated, cell-free varicella-zoster virus (VZV) vaccine that comprises: (a) Culturing VZV infection-susceptible cells, selected from human diploid cells, to confluency in monolayer culture, under conditions of sufficiently high nutrition to achieve a high degree of cell replication, and supplying a non-metabolizable disaccharide; (b) infecting the cells cultured according to step (a) at as close to the point of confluency as possible with as high a multiplicity of infection of VZV-infected cells as practical; (c) maintaining the VZV-infected culture in a state of high nutrition for about 22-96 hours and harvesting at the point of peak infectious VZV production; (d) washing the VZV-infected culture with a physiologic solution, optionally containing a lysosomotropic agent, such as ammonium chloride or chloroquine, prior to harvesting the VZV infected cells; (e) Harvesting the VZV infected cells into a minimal volume of a stabilizing solution and either disrupting the cells immediately or freezing the cells for later disruption, (1) Disrupting the VZV-infected cells to optimally release cell-associated VZV, and removing cellular debris, to provide a cell-free VZV preparation. The process is proposed for mass production of live vaccine. Appropriate nutrient medium for growing cells in monolayer culture in that connection is described as consisting essentially of SRFE-2 medium supplemented with between 0.2 mg/mL and 0.4 mg/mL soybean lipid and 10% fetal calf serum, the cells being selected from MRC-5 cells, WI-38 cells and Vero cells.

U.S. Pat. No. 5,665,362 (Cantab Pharmaceuticals Research: S C Inglis et al) and U.S. Pat. No. 5,837,261 (Cantab Pharmaceuticals Research: SC Inglis et al) disclose recombinant cells and culture methods for producing genetically disabled herpesvirus such as herpes simplex virus for vaccine purposes, wherein the virus is grown on complimentary cells.

U.S. Pat. No. 6,267,967 (Cantab: M D Johnston et al) describe processes for purification of herpes simplex virus. Infectious preparations of human herpesviruses such as herpes simplex virus (HSV), e.g. HSV type 2 (HSV-2), which tend to remain strongly cell-associated when grown in culture and affinity reagent carrying the virus, which can be applied from a carrier liquid containing salt (e.g. sodium chloride or other pharmaceutically acceptable salt over about 0.4M) or containing heparin or another sulfated or sulfonated polysaccharide (e.g. in the order of about 10-250, such as about 50, micro-g/mL), can then suitably be washed and the virus recovered in actively infectious form by elution, e.g. with high-concentration salt solution or with sulfated or sulfonated polysaccharide. The initial harvesting of virus from such a cell culture can be carried out in any of a variety of ways. Examples of methods include cell rupture, e.g. by freeze-thaw cycles or osmotic stress procedures, e.g. with hypotonic saline or glycerol solutions, sonication, elution by heparin or dextran sulfate or equivalent, or by using elution with saline solution.

U.S. Pat. No. 6,013,265 (UMB: L Aurelian), incorporated herein by reference, or U.S. Pat. No. 6,054,131 (UMB: L Aurelian), incorporated herein by reference, disclose a growth compromised herpes simplex recombinant virus, e.g.

HSV-2, in which the PK domain has been deleted. In a wild type HSV-2 virus, replication began at 2 hours post-infection and reached peak levels at 36 hrs post-infection. In the PK deleted HSV-2, the onset of replication was not seen until 15 hrs post-infection both in 10% serum and 0.5% serum supplemented Vero cells. When replication resumed this mutant reached titers similar to those of HSV-2 at 36 hrs post infection in the presence of 10% serum, but not in cells supplemented with in 0.5% serum in the medium.

It remains desirable to provide methods for production of herpesvirus-containing preparations, capable of contributing to the manufacture of infectious virus preparations in good yield and purity, e.g. those that are to be used in vaccines or as therapies.

BRIEF SUMMARY OF THE INVENTION

Embodiments of the invention include processes for preparing herpesvirus for a vaccine or therapy, which comprise (a) culturing host cells infected with the virus, and (b) separating of the medium from the infected cells and (3) using the supernatant to provide a virus preparation suitable for immunotherapy or vaccination of an animal.

It is, accordingly, an objective of embodiments of the present invention to provide processes for the isolation of herpesvirus for use in a vaccine or therapy.

Another objective of embodiments of the present invention to provide processes for the isolation of herpesvirus which are simple, inexpensive, and easy to implement.

Another objective of embodiments of the present invention to provide processes for the isolation of herpesvirus which do not involve the addition of additives to aid in purification.

Another objective of embodiments of the present invention to provide processes for the isolation of herpesvirus which do not require the disruption of cells used to produce the herpesvirus.

Another objective of embodiments of the present invention to provide processes for the isolation of herpesvirus which utilize only inexpensive components.

Another objective of embodiments of the present invention to provide processes for the growth of herpesvirus which are performed in the absence of serum.

Another objective of embodiments of the present invention to provide processes for the isolation of herpesvirus which are performed in the absence of serum A final objective of embodiments of the present invention to provide processes for the isolation of herpesvirus which involve easy to obtain and inexpensive reagents and are without adverse effects on the environment.

BRIEF DESCRIPTION OF THE SEVERAL VIEWS OF THE DRAWING

Not Applicable.

DETAILED DESCRIPTION OF THE INVENTION

We have found, most surprisingly, that an HSV-2 which has been deleted in the PK domain is readily transferred beyond the cell wall of the cell wherein it has been grown and is found in abundance in the culture fluid as well as in the cell. Virus levels in each area are found to be within 1 log of the levels of the other and since the supernatant contains 30-300 times, more or less, volume than does the cell mass, the available level of virus is substantially higher in the supernatant than in the cell. This obviates the need for cell rupture to free the virus particle found normally within the infected cell. Cell rupture has the disadvantages of requiring extensive purification of impurities consisting of cellular components and of reagents added to effect cell rupture.

Again, most surprisingly, we have found that cellular media which is serum free is compatible with growth of an HSV-2 which has been deleted in the PK domain, even though this mutant had previously been shown to be growth compromised in medium containing 10% fetal calf serum and not reproductive in medium containing 0.5% fetal calf serum.

In embodiments of the invention, suitable media for virus production include, for example, EMEM with 10% serum, or for example, VP-SFM (Invitrogen, Bethesda, Md.) which has a very low protein concentration (5 μg/mL and contains no proteins or peptides of animal or human origin) but does contain human recombinant epidermal growth factor (EGF) and recombinant human insulin or, as an example, RenCyte (In Vitro Services and Systems, Göttingen, Germany), which has no protein or serum. Other commercially available media that could be used, for example, include PC-1 or HL-1 (Cambrex Bioscience, Walkersville, Md.) which have added insulin.

In embodiments of the invention, cell lines which support the limited growth of PK deleted recombinant HSV-2 include cells mentioned in U.S. Pat. No. 6,013,265 (UMB: L Aurelian) or U.S. Pat. No. 6,054,131 (UMB: L Aurelian) and most preferably are Vero or MRC-5 cells.

In embodiments of the invention, a much higher degree of purity is obtained by use of the cell supernatant as opposed to rupturing the cells, since contaminating proteins are retained within the cell, and ICP10deltaPK allows a very high concentration of viral particles in the cell growth medium, e.g. up to $10^9$ pfu/mL.

In embodiments of the invention affinity purification can typically be carried out on a virus supernatant that has been obtained from a culture of suitably infected host cells such as Vero cells or MRC-5. It can be convenient to pass such an initially-harvested viral preparation through a membrane filter, e.g. on approximately 5 micron or finer membrane filter, to yield a clarified viral suspension, before the affinity purification. Using examples of the invention e.g. as described below, it is possible to prepare viral fractions containing usefully reduced levels of DNA and protein relative to the virus titer. The viral product of the affinity purification can if desired be subjected to any further chosen purification steps. The virus preparation harvested in this way can be treated with nuclease enzyme either before (or less preferably after) the affinity purification, to reduce any content of contaminating nucleic acid to acceptable levels. The virus preparations obtained by the use of processing steps as described herein can be further processed and made part of pharmaceutical compositions, e.g. with per-se conventional ingredients of virus vaccines or other pharmaceutically acceptable agents useful in stabilizing herpevirus. The invention is further described and illustrated by the following non-limitative example.

EXAMPLE 1

A process according to an example of the invention, for harvesting and purifying virus particles, can make use of a culture of Vero cells infected with HSV-2 (e.g. a PK deleted mutant of HSV2 as described in U.S. Pat. No. 6,013,265 (UMB: L Aurelian) or U.S. Pat. No. 6,054,131 (UMB: L Aurelian) for vaccine use), and grown essentially in known manner in 10% serum with Eagle's minimum essential medium (EMEM) supplemented with 10% fetal calf serum (FCS) and antibiotics. Confluent Vero cells were infected with HSV-2, ICP10deltaPK (CS) at a multiplicity of infection of about 0.01 and incubated at about 34° C. When cytopathic effect is observed to be 80-100%, e.g. 24-72 hours after infection, the culture can be treated as ready for virus harvest.

Alternatively, the Vero cells can be infected with HSV-2 and grown as directed in a serum free medium such as VP SFM from Invitrogen, Bethesda, Md. or RenCyte (In Vitro Services and Systems, Göttingen, Germany).

To harvest the virus, the culture medium is decanted and used directly or purified further. Levels of virus using RenCyte or VP-SFM are also suitable for use. The medium containing the virus can then be used directly to immunize for pharmaceutical use, stabilized with stabilization agents or may be further purified.

For example, pre-filtration can be carried out e.g. with a filter having a pore size in the range from 0.4-5 micron (not critical) to yield a clarified viral suspension, before further affinity purification. The supernatant liquid from centrifugation can be diluted or diafiltered to obtain suitable ion concentrations.

The culture medium may optionally be treated with a nuclease enzyme (Benzonase™ which has DNase activity, and RNase activity) at up to about 50 units/mL in the presence of about 2-10 mM magnesium ion, e.g. for up to about 1 hour at a temperature from about 4° C. up to room temperature. However, it can often be found that the culture medium has a sufficiently low content of DNA that a separate DNase treatment step is unnecessary.

The virus-containing liquid may be further purified on a Pharmacia heparin HP column chromatography material (based on a highly cross-linked agarose gel) (e.g. of diameter about 34 micron) obtainable from Pharmacia Biotech in the form of HiTrap™ prepared columns. Alternatively, the affinity reagent can be beads of Fractogel™ FMD $SO_5$ 650 M from Merck (Darmstadt) as described above, used in generally similar manner.

In a further example of this step, a HSV-2 virus culture supernatant could be applied to a heparin column prepared by washing with phosphate buffered saline. Approximately 100 mL of virus preparation containing as much as $10^8$ pfu/mL might be loaded on to the column. The virus could be fractionally eluted and the fractions containing the concentrated virus could be collected.

If desired, as an optional further purification step, the intermediate virus-containing eluate from the column could be subjected to tangential cross-flow filtration (diafiltration) e.g. using a filter/membrane with a 500 kD exclusion limit in a Filtron™ or other tangential crossflow device.

The retentate from the cross-flow ultrafiltration step could optionally, if desired, be treated by diafiltration against citrate/saline buffer, and the retentate finally subjected to 0.2 micron (sterilizing) filtration optionally preceded by filtration with a filter of from about 0.45 micron to 5 micron, using the same buffer again.

If desired, this step can be used to make the liquid containing the virus preparation up to about 20 mg/mL in a suitable stabilizer such as a stabilizing protein, e.g. human serum albumin at about 20 mg/mL. It can sometimes be useful to prewash the filters with a liquid containing the same stabilizer in the same buffer, before using the filters to treat the virus preparation.

The resulting product can be obtained as a suspension of virus particles in a stabilizer, in which the level of residual DNA can be satisfactorily low.

The invention can be usefully applied, for example to the culture and harvesting of a recombinant HSV-2 virus for vaccine use, which virus has a deletion in respect to the PK gene and has been cultured on a cell line of Vero cells or MRC 5 cells.

The present invention and disclosure extend to the methods and compositions and the resulting products as described herein, and to modifications and variations of the steps and features mentioned and described in the present description and claims, including all combinations and sub-combinations of the steps and features hereof, including variations in the order and selection of steps, and the documents cited herein are hereby incorporated by reference in their entirety for all purposes.

We claim:

1. A process for preparing a recombinant herpesvirus for a vaccine or therapy, which comprises:

(a) culturing host cells, selected from the group of host cells consisting of Vero, or MRC5 cells, infected with the virus, (b) separating the medium from the infected cells and (c) using the separated virus containing medium for further purification, immunotherapy or vaccination of an animal.

2. The process of claim 1 in which said host cells are selected from the group consisting of Vero and MRC5 cells.

3. The process of claim 1 in which said host cells are Vera cells.

4. The process of claim 1 wherein said herpesvirus is an HSV-2 which has the PK domain deleted.

5. The process of claim 1 wherein said herpesvirus is ICP10deltaPK.

6. The process of claim 1 wherein said culture is carried out in a serum free medium.

7. The process of claim 1 wherein said culture is carried out in a medium containing about 5 µg/mL protein or less.

8. The process of claim 1 where said culture is carried out in a medium with added epidermal growth factor.

9. The process of claim 1 where said culture is carried out in a medium with added insulin.

10. A process according to claim 1, further comprising the step:

(d) formulating said herpesvirus with a pharmaceutically acceptable carrier, excipient or stabilizing agent.

11. A process according to claim 1 further comprising the step:

(e) sterilizing and freezing or freeze-drying the preparation.

12. A process according to claim 1 wherein the herpesvirus comprises infectious herpesvirus.

13. A process according to claim 1 wherein the resulting pharmaceutical formulation is for use as an immunotherapy.

14. A process for growing recombinant herpesvirus comprising the step:

(a) culturing host cells, selected from the group of cells consisting of Vero, or MRC5 cells, infected with the virus in a serum free medium.

15. The process of claim 14 in which said host cells are selected from the group consisting of Vero and MRC5 cells.

16. The process of claim 14 in which said host cells are Vero cells.

* * * * *